United States Patent [19]

Kussendrager et al.

[11] Patent Number: 4,802,926
[45] Date of Patent: Feb. 7, 1989

[54] SPRAY DRIED LACTOSE AND PROCESS FOR PREPARING THE SAME

[75] Inventors: Klaas D. Kussendrager; Henricus A. M. van den Biggelaar, both of Veghel; Herman Vromans, Een, all of Netherlands

[73] Assignee: DMV-Campina B.V., GE Veghel, Netherlands

[21] Appl. No.: 27,424

[22] Filed: Mar. 18, 1987

[30] Foreign Application Priority Data

Mar. 21, 1986 [NL] Netherlands ................. 8600731

[51] Int. Cl.⁴ .............................................. C13K 5/00
[52] U.S. Cl. .................................... 127/31; 127/15
[58] Field of Search ................................. 127/31, 15

[56] References Cited

U.S. PATENT DOCUMENTS

| | | | |
|---|---|---|---|
| 2,088,606 | 8/1937 | Peebles et al. | 127/31 |
| 3,639,170 | 2/1972 | Hutton et al. | 127/31 |
| 3,802,914 | 4/1974 | Nczbed | 127/61 |

*Primary Examiner*—W. J. Shine
*Assistant Examiner*—Chung K. Pak
*Attorney, Agent, or Firm*—Scully, Scott, Murphy & Presser

[57] ABSTRACT

The invention relates to a spray dried lactose suitable for use as component of tablets and to a process for preparing same. The lactose is predominantly crystalline and contains at most 50% by weight of amorphous lactose. At least 50% by weight of the crystalline lactose consists of particles below 50 μm. The preparation process comprises a step of suspending crystalline alpha-lactose hydrate at 0°–90° C. in a saturated lactose solution, and a spray drying step. The temperature of the suspension is kept substantially constant until the time of spray drying in order to minimize crystallization and dissolution events.

2 Claims, No Drawings

SPRAY DRIED LACTOSE AND PROCESS FOR PREPARING THE SAME

This invention relates to spray dried lactose products having improved properties for making tablets and a process for manufacturing such products. U.S. Pat. No. 3,639,170 discloses the manufacture of lactose products by spray drying which comprises atomizing a slurry of lactose crystals in a lactose solution in a spray dryer. The slurry of crystals may then be prepared by crystallization of a concentrated lactose solution which has a temperature of 80°–65° C. and is cooled to 45°–30° C. by addition of about 1% by weight of lactose seed crystals having an average size of 5 μm.

The major part of the crystals thus formed ranges in size from 50 to 100 μm, preferably at least 60% of the lactose in the slurry is in this form. In practice, there is spray dried a slurry having 75–85% of the lactose in crystalline form. An alternative manufacturing process starts from ground lactose which is suspended in water so that a part of it goes into solution, but with no less than 80–90% of the lactose present remaining in the form of the above crystals of substantially 50–100 μm during the spray drying step. The spray drying step then results in a product consisting of substantially spherical particles of 80–250 μm. These particles contain the lactose substantially in the form of crystals of 50–100 μm surrounded and bonded together by lactose in amorphous form.

As special advantages of this form of lactose reference is made to its improved solubility and its more favourable flow characteristics. In the manufacture of tablets in high-speed tableting equipments the step of faster filling the tableting dies is of advantage to this granular spherical lactose product.

The tablets which can be made from this lactose product disclosed in U.S. Pat. No. 3,639,170 are not further distinguished over tablets made with other lactose porducts spray dried or obtained by direct crystallization, as far as the properties of these tablets are concerned. By conventional testing methods a crush resistance of mostly 4–6 kg is measured in tablets of 500 mg having a diameter of 13 mm, which tablets are formed from these known spray dried lactose products at a compaction load of 1 ton.

It has now been found that tablets can be made on the basis of lactose with addition of pharmaceutically active substances or other substances conventional in tablets with a crush resistance of 6–20 kg, if there is started from spray dried lactose in which not more than 50% is in amorphous form, and in which at least 50% of the crystalline part of the lactose consists of particles less than 50 μm. More in particular, tablets with a crush resistance of 10–20 kg can be obtained if 50% or more of the crystalline part of the lactose consists of crystals less than 16 μm to at least 50% by weight.

It has been found that within the above range the crush resistance of tablets made from spray dried lactose with a constant amorphous lactose content is higher as the primary crystalline particles in the spherical spray dried particles are smaller.

In known processes for manufacturing spray dried lactose such a fineness of the primary crystalline particles in the spray dried spherical particles is not obtained in general. In fact, if a concentrated lactose solution is started from, to which there is added, e.g., about 1% by weight of seed lactose crystal having a size of 5 μm on the average, and in which crystallization then takes place by cooling, most of the crystals grow to sizes larger by many times than those of the seed material, i.e. also considerably larger than is desired for the primary particles required for this invention. If, alternatively, a finely ground lactose product is started from, which is suspended in water in a known manner, especially the finest particles will first pass into solution, so that exactly the coarsest particles remain in the slurry. In spray drying such a slurry the lactose concentration in the drying, sprayed droplets rapidly increases, and also then there is little opportunity for the lactose which in the slurry is in a dissolved state to pass into the crystalline state.

Consequently, in the spray dried product the content of crystalline lactose will in the first instance correspond to the amount of crystal in the slurry before drying, and the dissolved part of the slurry will substantially be found in the spray dried product as amorphous lactose. In consequent thereof the primary crystals in the spray dried particles are nearly always as large as or larger than the crystals in the slurry.

Accordingly, for manufacturing lactose products according to this invention it is necessary to adjust both the ratio between dissolved and crystalline lactose and the sizes of the crystals in the slurry at the moment of spraying to values corresponding to the values required in the dry product.

The required sizes of the crystals in the slurry to be spray dried according to this invention are obtained in a known manner by either recovering from coarse crystals by grinding and/or screening a fine fraction having sizes less than or equal to the required sizes of the primary crystalline particles in the contemplated product, or crystallizing in a likewise known manner, a solution to form such a fine crystal and separating the mother liquor.

The required ratio between amorphous and crystalline lactose is then obtained by suspending these crystals having known sizes in a saturated or practically saturated lactose solution at a temperature within the range of 0° C. to 90° C. and keeping this temperature so constant up to the moment of spray drying as to enable no substantial crystallization or dissolution. The selection of the ratio between the amounts of crystalline material and dissolved lactose in the slurry determines the ratio between the amounts of crystalline and amorphous lactose in the spray dried product.

By thus manufacturing a spray dried lactose product having a controlled ratio between amorphous and crystalline lactose and a controlled particle size of the primary crystalline particles, a product is obtained which combines the already known properties of a faster solubility and improved flow characteristics with new favourable properties in the making of tablets.

It is a special advantage of this invention that thus more solid tablets, e.g., for use in the pharmaceutical industry, can be made with no change of formulation being required. In fact, the improved properties are obtained with a substance having the same chemical composition as previously used, and having the same physical characteristics in all relevant respects, such as powder-flow characteristics. The formulation of the pharmaceutical product requires no change, and yet the tablets are less subject to crushing.

This invention will further be illustrated by the following examples.

EXAMPLE 1

Of a comminuted alpha-lactose hydrate fractions having different sizes were obtained by screening. The screening fractions of 1-3 μm, 8-16 μm, 16-24 μm, 24-32 μm, 32-45 μm were suspended in saturated lactose solutions. The amount of solution in proportion to the amount of crystal was so varied as to obtain after drying respectively 15-21% about 30%, and about 50% amorphous lactose in the dry product. The products thus obtained after spray drying were tableted in different ways. Without addition of lubricants or active components and without pre-granulated tablets of each 500 mg lactose having a diameter of 13 mm could be formed at a compaction load of 1 respectively which tablets were tested for crush resistance by means of a crush resistance tester of the Schleuniger Model 2E type. The results are listed in Table 1.

The finer the screening fraction chosen the higher the measured crush resistances.

Also the content of amorphous lactose in the tableted product proves to be important to the strength of the obtained tablet. A specific selection of the starting material proves to enable a considerably stronger variation of the strength of the tablets obtained than was possible with the hitherto conventional forms of spray dried lactose.

TABLE 1

| content amorphous | screening fraction | crush resistance kg |
|---|---|---|
| 15% | 1-8 μm | 15.6 |
| 15% | 8-16 μm | 10.9 |
| 15% | 16-24 μm | 8.5 |
| 15% | 24-32 μm | 6.8 |
| 15% | 32-45 μm | 6.5 |
| 30% | 1-8 μm | 18.2 |
| 30% | 8-16 μm | 11.6 |
| 30% | 16-24 μm | 9.2 |
| 30% | 24-32 μm | 7.8 |
| 30% | 32-45 μm | 6.5 |
| 50% | 1-8 μm | 16 |
| 50% | 8-16 μm | 10.0 |
| 50% | 16-24 μm | 9.4 |
| 50% | 24-32 μm | 7.2 |
| 50% | 32-45 μm | 6.5 |

EXAMPLE 2

A filtered discoloured lactose solution having a 59% dry solid content of 90° C. was cooled, which temperature was decreased to 28° C. within 2 hours. Comminuted lactose crystal in an amount of 0.4% was added as a seed material. When the refraction did not show any further decrease by crystallization, the mass was spray dried, and a product was obtained which according to analysis contained 4.2% crystal water and 0.7% otherwise bound water.

The product therefore contained about 84% by weight of crystalline material and 16% by weight of amorphous lactose, wherein 5.3% by weight of beta lactose A microscopic examination showed that the crystals in the spray dried paricles had sizes of the order of 20 μm.

This product was formed into 13 mm tablets of 500 mg at a compaction load of 1 ton. In a crush resistance tester a crush resistance of 9.0 kg was measured.

EXAMPLE 3

A pharmaceutical lactose ground to trade size "500 mesh" (30 μm and less) was suspended in lactose solutions having progressive lactose contents and corresponding temperatures. The granular size distribution of the starting material and the slurries was established by means of a Coulter Counter. The slurries were spray dried with the temperature being carefully kept constant.

In the dried products the content of crystal water and otherwise bound water as well as the ratio between the different lactose forms were determined. Also, tablets of 500 mg lactose having a diameter of 13 mm were formed at 1 ton compaction load, and then the crush resistance was measured. The results are listed in the following table. A microscopic verification showed that the crystals in the spray dried particles had sizes of about 16-20 μm.

TABLE 2

| | Starting Material | Spray dried products | | |
|---|---|---|---|---|
| | | S-1 | S-2 | S-3 |
| % Crystalline | 100 | 82 | 70 | 60 |
| % Amorphous | — | 18 | 30 | 40 |
| % Beta lactose | — | 9.8 | 16.7 | 26.1 |
| Granular size | | | | |
| % less than 12.6 μm | 38.0 | 31.5 | 23.0 | 17.0 |
| % less than 15.9 μm | 52.0 | 48.0 | 34.0 | 30.0 |
| % less than 20 μm | 73.0 | 70.0 | 49.0 | 52.0 |
| % less than 25.2 μm | 92.5 | 90.0 | 70.0 | 80.5 |
| Crush resistance kg (of tablet 500 mg, diam. 13 mm, 1 ton) | — | 11.8 | 12.4 | 11.3 |

What we claim:

1. Spray dried lactose products obtained by feeding a slurry of crystalline alpha-lactose hydrate in a saturated lactose solution to a spray dryer and drying the same, characterized in that from about 15 to about 50% by weight of the spray dried lactose is in amorphous form and at least 50% by weight of the lactose is in crystalline form, the crystalline particle size being less than about 45 micrometers.

2. Spray dried lactose products as claimed in claim 1, characterized in that at least 50% by weight of the crystalline lactose particle size is less than 16 micrometers.

* * * * *

UNITED STATES PATENT AND TRADEMARK OFFICE
CERTIFICATE OF CORRECTION

PATENT NO. : 4,802,926

DATED : February 7, 1989

INVENTOR(S) : Klaas D. Kussendrager, et al.

It is certified that error appears in the above-identified patent and that said Letters Patent is hereby corrected as shown below:

In the Abstract, line 6: "below 50 μm" should read as --below 50 μm or micrometer--

Column 1, line 15: "5 μm" should read as --5 μm or micrometer--

Column 1, line 17: "100 μm" should read as --100 μm or micrometer--

Column 1, line 24: "100 μm" should read as --100 μm or micrometer--

Column 1, line 27: "250 μm" should read as --250 μm or micrometer--

Column 1, line 29: "100 μm" should read as --100 μm or micrometer--

Column 1, line 40: "porducts" should read as --products--

Column 1, line 68: "5 μm" should read as --5 μm or micrometer--

UNITED STATES PATENT AND TRADEMARK OFFICE
CERTIFICATE OF CORRECTION

PATENT NO. : 4,802,926

DATED : February 7, 1989

INVENTOR(S) : Klaas D. Kussendrager, et al.

It is certified that error appears in the above-identified patent and that said Letters Patent is hereby corrected as shown below:

Column 3, line 5: "1-3 $\mu$m, 8-16 $\mu$m, 16-24 $\mu$m, 24-32 $\mu$m, 32-45 $\mu$m" should read as --1-3 $\mu$m or micrometer, 8-16 $\mu$m or micrometer, 16-24 $\mu$m or micrometer, 24-32 $\mu$m or micrometer, 32-45 $\mu$m or micrometer--

Column 4, line 6: "20 $\mu$m" should read as --20 $\mu$m or micrometer--

Column 4, line 13: "30 $\mu$m" should read as --30 $\mu$m or micrometer--

Column 4, line 28: "20 $\mu$m" should read as --20 $\mu$m or micrometer--

Signed and Sealed this

Tenth Day of October, 1989

Attest:

DONALD J. QUIGG

*Attesting Officer*  *Commissioner of Patents and Trademarks*